United States Patent [19]
Flier et al.

[11] Patent Number: 5,223,425
[45] Date of Patent: Jun. 29, 1993

[54] DNA ENCODING HUMAN ADIPSIN WITH COMPLEMENT D ACTIVITY

[75] Inventors: Jeffrey S. Flier; Bruce M. Spiegelman, both of Newton; Barry M. Rosen, Boston, all of Mass.; R. Tyler White, Fremont, Calif.

[73] Assignee: The Beth Israel Hospital Association, Boston, Mass.

[21] Appl. No.: 277,963

[22] Filed: Nov. 30, 1988

Related U.S. Application Data

[63] Continuation-in-part of Ser. No. 34,203, Apr. 2, 1987, abandoned.

[51] Int. Cl.$^5$ .......................... C12N 5/10; C12N 1/21; C12N 1/19; C12N 15/12
[52] U.S. Cl. ............................. 435/240.2; 435/252.3; 435/252.33; 435/255; 435/256; 435/320.1; 536/23.2
[58] Field of Search ................. 435/252.3, 69.1, 172.3, 435/320.1, 183; 536/27

[56] References Cited

PUBLICATIONS

Min et al. 1986 Nucleic Acids Research 14:8879.
Cook et al. 1985. Proc. Natl. Acad. Sci USA 82:6480.
Spiegelmane et al 1983 J. Biol. Chem. vol. 258:10083.
Suggs et al Proc. Natl. Acad. Sci. USA 78:6613 Use of Synthetic Oligonucleotides.
Naniatis et al. 1982 Cold Spring Harbor Lab., Molecular Cloning: A Lab. Manual.
Niemann et al., Biochemistry 23:2482 1984.

*Primary Examiner*—Richard A. Schwartz
*Assistant Examiner*—J. Le Guyader
*Attorney, Agent, or Firm*—Lorusso & Loud

[57] ABSTRACT

The invention provides a recombinant purified human protein in substantial quantities which has both adipsin and complement D activity. The invention also provides materials and methods to produce the protein. In addition, antibodies immunoreactive with this protein are useful to diagnose metabolic defects attributable to adipsin deficiency or complement D deficiency. The protein can be used to treat obesity caused by adipsin deficiency or to treat subjects for infection.

9 Claims, 18 Drawing Sheets

```
pHG31 vs human complement D 20        30        40        50        60        70        80
AACAAPPRGRILGGREAEAHARPYMASVQLNGAHLCAGVLVAEQWVLSAAHCLEDAADGKVQVLLGAHSL
              ::::::::::::::::::::::::  ::::::::::::::::::::::::::::::: :
             ILGGREAEAHARPYMASVQLNGAHLCGGVLVAEQWVLSAAHCLEDAADGKVQVLLGATHL
           X        10        20        30        40        50        60

90       100       110       120       130       140       150
SQPEPSKRLYD-VLRAVPHPDSQPDTIDHDLLLLQLSEKATLGPAVRPLPVQRVDRDVAPGTLCDVAGWG
::::        ::::::::::::::::::::::::::::::::::::::::::::::::::::::::
PQPEPXXXITIEVLRAVPHPDSQPDTIDHDLLLLQLSEKATLGPAVRPLPVQRVDRDVAPGTLCDVAGWG
           70        80        90       100       110       120       130

160       170       180       190       200       210       220
IVNHAGRRPDSLQHVLLPVLDRATCNRRTHHDGAITERLMCAESNRRDSCKGDSGGPLVCGGVLEGVVTS
::::::::::::::::::::::::::::                ::::::::::::::::::::::::::
IVNHAGRRPDSLQHVLLPVLDRATCRLYDVL------RLMCAESNRRDSCKGDSGGPLVCGGVLEGVVTS
          140       150       160                 170       180       190

230       240       250X
GSRVCGNRKKPGIYTRVASYAAWIDSVLA.
::::::::::::::::::: ::::::  ::
GSRVCGNRKKPGIYTRVATYAAWIDHVL.
          200       210       220 X
```

```
        BamHI
        GGATCCCACC ATG CAC AGC TCC GTG TAC TTC GTG GCT CTG GTG ATC CTG GGA GCG    54
                   MET His Ser Ser Val Tyr Phe Val Ala Leu Val Ile Leu Gly Ala

GCT GTA TGT GCA GCA CAG CCC CGA GGC CGG ATT CTG GGT GGC CAG GAG GCC GCA  108
        Ala Val Cys Ala Ala Gln Pro Arg Gly Arg Ile Leu Gly Gly Gln Glu Ala Ala

GCC CAT GCT CGG CCC TAC ATG GCT TCC GTG CAA GTG AAC GGC ACA CAC GTG TGC  162
        Ala His Ala Arg Pro Tyr MET Ala Ser Val Gln Val Asn Gly Thr His Val Cys

GGT GGC ACC CTG CTG GAC GAG CAG TGG GTG CTC AGT GCT GCA CAC TGC ATG GAT  216
        Gly Gly Thr Leu Leu Asp Glu Gln Trp Val Leu Ser Ala Ala His Cys MET Asp

GGA GTG ACG GAT GAC GAC TCT GTG CAG GTG CTC CTG GGT GCC CAC TCC CTG TCC  270
        Gly Val Thr Asp Asp Asp Ser Val Gln Val Leu Leu Gly Ala His Ser Leu Ser

GCC CCT GAA CCC TAC AAG CGA TGG TAT GAT GTG CAG AGT GTA GTG CCT CAC CCG  324
        Ala Pro Glu Pro Tyr Lys Arg Trp Tyr Asp Val Gln Ser Val Val Pro His Pro
```

FIG. 1A

```
                                                351                            378
GGC AGC CGA CCT GAC AGC CTT GAG GAC CTC ATT CTT TTT AAG CTA TCC CAG
Gly Ser Arg Pro Asp Ser Leu Glu Asp Leu Ile Leu Phe Lys Leu Ser Gln 405                            432
AAT GCC TCG TTG GGT CCC CAC GTG AGA CCC CTA CCC TTG CAA TAC GAG GAC AAA
Asn Ala Ser Leu Gly Pro His Val Arg Pro Leu Pro Leu Gln Tyr Glu Asp Lys 459                            486
GAA GTG GAA CCC GGC ACG CTC TGC GAC GTG GCT GGT TGG GGT GTG GTC ACC CAT
Glu Val Glu Pro Gly Thr Leu Cys Asp Val Ala Gly Trp Gly Val Val Thr His

StuI                                    513                            540
GCA GGA CGC AGG CCT GAT GTC CTG CAA CTC CAT CAA CTC AGA GTG TCA ATC ATG AAC CGG
Ala Gly Arg Arg Pro Asp Val Leu Gln Leu His Gln Leu Arg Val Ser Ile MET Asn Arg 567                            594
ACA ACC TGC AAT CTG CGC ACG TAC CAT GAC GGG GTA GTC ACC ATT AAC ATG ATG
Thr Thr Cys Asn Leu Arg Thr Tyr His Asp Gly Val Val Thr Ile Asn MET MET 621                            648
TGT GCA GAG AGC AAC CGC AGG GAC ACT TGC AGG GGA GAC TCC GGC AGC CCT CTA
Cys Ala Glu Ser Asn Arg Arg Asp Thr Cys Arg Gly Asp Ser Gly Ser Pro Leu
```

FIG. 1B

```
                                                        675
GTG TGC GGG GAT GCA GAA GGT GTC GTT ACG TGG GGC TCT CGC GTC TGT GGC
Val Cys Gly Asp Ala Val Glu Gly Val Val Thr Trp Gly Ser Arg Val Cys Gly
                                                                        702

729
AAT GGC AAA AAG CCG GGC GTC TAT ACC CGA GTG TCA TCC TAC CGG ATG TGG ATC
Asn Gly Lys Lys Pro Gly Val Tyr Thr Arg Val Ser Ser Tyr Arg MET Trp Ile
                                                                        756

783
GAA AAC ATC ACA AAT GGT AAC ATG ACA TCC TGA GGG GAC ACC AGA GAC ACG TGG
Glu Asn Ile Thr Asn Gly Asn MET Thr Ser End
                                                                        810

837                                    BamHI
CTC AGG GAA ACA GAA GAC ACG TGG CTC ACA ATA AAT GCA TGC ATC TGGGATCC
```

FIG.1C pHG31
EcoRI
AAT TCG GGC GCA GTT CTG GTC CTA GGA GCG GCC GCC TGC GCG CCG     54
Asn Ser Gly Ala Val Leu Val Leu Gly Ala Ala Ala Cys Ala Pro
                                 NotI

BamHI
CCC CGT GGT GGC ATC CTG GGC GGA AGA GAG GCC GAG GCG CAC CGG CCC TAC    108
Pro Arg Gly Gly Ile Leu Gly Gly Arg Glu Ala Glu Ala His Arg Pro Tyr

ATG GCG TCG GTG CTG CAG CTG AAC GGC CAC CTG TGC GCA GGC GTC CTG GCG    162
MET Ala Ser Val Gln Leu Asn Gly His Leu Cys Ala Gly Val Leu Ala

GAG CAG TGG GTG CTG AGC GCC GCG CAC TGC CTG GAG GAC GCC GAC GGG AAG    216
Glu Gln Trp Val Leu Ser Ala Ala His Cys Leu Glu Asp Ala Ala Asp Gly Lys

GTG CAG GTT CTC CTG GGC GCC CAC TCC CTG TCG CAG CCG GAG CCC TCC AAG CGC    270
Val Gln Val Leu Leu Gly Ala His Ser Leu Ser Gln Pro Glu Pro Ser Lys Arg

CTG TAC GAC GTG CTC CGC GCA GTG CCC CAC CCG GAC AGC CAG CCC GAC ACC ATC    324
Leu Tyr Asp Val Leu Arg Ala Val Pro His Pro Asp Ser Gln Pro Asp Thr Ile

FIG.2A

```
                                                            351                                                378
GAC CAC GAC CTC CTG CTA CAG CTG TCG GAG AAG GCC ACA CTG GGC CCT GCT
Asp His Asp Leu Leu Leu Gln Leu Ser Glu Lys Ala Thr Leu Gly Pro Ala 405                                                432
GTG CGC CCC CTG CCC TGG CAG CGC GAC GTG GCA CCG GGA ACT CTC
Val Arg Pro Leu Pro Trp Gln Arg Asp Val Ala Pro Gly Thr Leu 459                                                486
TGC GAC GTG GCC GGC ATA GTC AAC CAC GCG GGC CGC CCG GAC AGC
Cys Asp Val Ala Gly Ile Val Asn His Ala Gly Arg Arg Pro Asp Ser

PstI                                                        513                                                540
CTG CAG CAC GTG CTC TTG CCA GTG CTG GAC CGC GCC ACC TGC AAC CGG CGC ACG
Leu Gln His Val Leu Leu Pro Val Leu Asp Arg Ala Thr Cys Asn Arg Arg Thr 567                                                594
CAC CAC GAC GGC GCC ATC ACC GAG CGC TTG ATG TGC GCG GAG AGC AAT CGC CGG
His His Asp Gly Ala Ile Thr Glu Arg Leu MET Cys Ala Glu Ser Asn Arg Arg 621                                                648
GAC AGC TGC AAG GGT GAC TCC GGG GGC CCG CTG GTG TGC GGG GGC GTG CTC GAG
Asp Ser Cys Lys Gly Asp Ser Gly Gly Pro Leu Val Cys Gly Gly Val Leu Glu
```

FIG.2B

```
                                                                    675
GGC GTG GTC ACC TCG GGC TCG CGC GTT TGC GGC AAC CGC AAG AAG CCC GGG ATC
Gly Val Val Thr Ser Gly Ser Arg Val Cys Gly Asn Arg Lys Lys Pro Gly Ile
                                                                    702

729
TAC ACC CGC GTG GCG AGC TAT GCG GCC TGG ATC GAC AGC GTC CTG GCC TAG GGT
Tyr Thr Arg Val Ala Ser Tyr Ala Ala Trp Ile Asp Ser Val Leu Ala End
                                                                    756

783
GCC GGG GCC TGA AGG TCA CCC AAG CAA CAA AGT CCC GAG CAA TGA AGT
                                                                    810

837
CAT CCA CTC CTG GTT GGT CTT TAT TGA GCA CCT ACT ATA TGC AGA AGG
                                                                    864

891
GGA GGC CGA GGT GGG AGG ATC ATT GGA TCT CAG GAG TTG GAG ATC AGC ATG GGC
                                                                    918

945
CAC GTA GCG CGA CTC CAT CTC TAC AAA TAA ATA AAA ATT AGC TGG GCA ATT GGC
                                                                    972

999
GGG CAT GGA GGT GGG TGC TTG TAG TTC CAG CTA CTC AGG AGG CTG AGG TGG GAG
                                                                    1026

1053 PstI
GAT GAC TTG AAC GCA GGA GGC TGA GGT TGC AGT GAG TTG TGA TTG CAC CAC TGC
                                                                    1080
  EcoRI
CCT CCC CGA ATT C
```

FIG.2C pHG31 vs human complement D

```
            20        30        40        50        60        70        80
AACAAPPRGRILGGREAEAHARPYMASVQLNGAHLCAGVLVAEQWVLSAAHCLEDAADGKVQVLLGAHSL
 :::::::::::::::::::::::::::::::: :::::::::::::::::::::::::::::::::: :
  ILGGREAEAHARPYMASVQLNGAHLCGGVLVAEQWVLSAAHCLEDAADGKVQVLLGATHL
X         10        20        30        40        50        60

90       100       110       120       130       140       150
SQPEPSKRLYTD-VLRAVPHPDSQPDTIDHDLLLLQLSEKATLGPAVRPLPVQRVDRDVAPGTLCDVAGWG
: :::        :::::::::::::::::::::::::::::::::::::::::::::::::::::::::
PQPEPXXXITIEVLRAVPHPDSQPDTIDHDLLLLQLSEKATLGPAVRPLPVQRVDRDVAPGTLCDVAGWG
       70        80        90       100       110       120       130

160       170       180       190       200       210       220
IVNHAGRRPDSLQHVLLPVLDRATCNRRTHHDGAITERLMCAESNRRDSCKGDSGGPLVCGGVLEGVVTS
::::::::::::::::::::::::::      :::::::::::::::::::::::::::::::::::::
IVNHAGRRPDSLQHVLLPVLDRATCRLYDVL------RLMCAESNRRDSCKGDSGGPLVCGGVLEGVVTS
      140       150       160       170       180       190

230       240       250X
GSRVCGNRKKPGIYTRVASYAAVIDSVLA.
:::::::::::::::::::: :: ::
GSRVCGNRKKPGIYTRVATYAAVIDHVL.
       200       210       220 x
```

FIG.3 pHG31-40

```
                                                                    54
GGAT CCC ACC ATG CAC AGC TCC GTG TAC TTC GCA GTT CTG GTC CTC CTA GGA GCG
          MET His Ser Ser Val Tyr Phe Ala Val Leu Val Leu Leu Gly Ala
          -24

27
                                                                   108
GCC GCC TGC GCC GCG CGG CCC CGT GGT CGG ATC CTG GGC GGC AGA GAG GCC GAG
Ala Ala Cys Ala Ala Arg Pro Arg Gly Arg Ile Leu Gly Gly Arg Glu Ala Glu
                         81        -1  +1

162
GCG CAC GCT CGG CCT TAC ATG GCG TCG GTG CAG CTG AAC GGC GCG CAC CTG TGC
Ala His Ala Arg Pro Tyr MET Ala Ser Val Gln Leu Asn Gly Ala His Leu Cys
                       135

216
GCA GGC GTC CTG GTG GCC GAG CGG TGG GTG CTG AGC GCG GCG CAC TGC CTG GAG
Ala Gly Val Leu Val Ala Glu Arg Trp Val Leu Ser Ala Ala His Cys Leu Glu
                       189

270
GAC GCG GCC GAC GGG AAG GTG CAG GTT CTC CTG GGC GCG CAC TCC CTG TCG CAG
Asp Ala Ala Asp Gly Lys Val Gln Val Leu Leu Gly Ala His Ser Leu Ser Gln
                       243
```

FIG.4A

```
                                                          297                                                               324
CCG GAG CCC TCC AAG CGC CTG TAC GAC GTG CTC CGC GCA GTG CCC CAC CCG GAC
Pro Glu Pro Ser Lys Arg Leu Tyr Asp Val Leu Arg Ala Val Pro His Pro Asp 351                                                               378
AGC CAG CCC GAC ACC ATC GAC CAC CTC CTG CTA CAG CTG TCG GAG AAG
Ser Gln Pro Asp Thr Ile Asp His Leu Leu Leu Gln Leu Ser Glu Lys 405                                                               432
GCC ACA CTG GGC CCT GCT GTG CGC CCC CTG CCC TGG CAG CGC GTG GAC CGC GAC
Ala Thr Leu Gly Pro Ala Val Arg Pro Leu Pro Trp Gln Arg Val Asp Arg Asp 459                                                               486
GTG GCA CCG GGA ACT CTC TGC GAC GTG GCC GGC ATA GTC AAC CAC GCG
Val Ala Pro Gly Thr Leu Cys Asp Val Ala Gly Ile Val Asn His Ala 513                                                               540
GGC CGC CCG GAC AGC CTG CAG CAC GTG CTC TTG CCA GTG CTG GAC CGC GCC
Gly Arg Pro Asp Ser Leu Gln His Val Leu Leu Pro Val Leu Asp Arg Ala
```

FIG.4B

```
     567                                                         594
ACC TGC AAC CGG CGC ACG CAC CAC GAC GGC GCC ATC ACC GAG CGC TTG ATG TGC
Thr Cys Asn Arg Arg Thr His His Asp Gly Ala Ile Thr Glu Arg Leu MET Cys 621                                                         648
GCG GAG AGC AAT CGC CGG GAC AGC TGC AAG GGT GAC TCC GGG GGC CCG CTG GTG
Ala Glu Ser Asn Arg Arg Asp Ser Cys Lys Gly Asp Ser Gly Gly Pro Leu Val 675                                                         702
TGC GGG GGC GTG CTC GAG GGC GTC ACC TCG GGC TCG CGC GTT TGC GGC AAC
Cys Gly Gly Val Leu Glu Gly Val Thr Ser Gly Ser Arg Val Cys Gly Asn 729                                                         756
CGC AAG AAG CCC GGG ATC TAC ACC CGC GTG GCG AGC TAT GCG GCC TGG ATC GAC
Arg Lys Lys Pro Gly Ile Tyr Thr Arg Val Ala Ser Tyr Ala Ala Trp Ile Asp 783                                                         810
AGC GTC CTG GCC TAG GGT GCC GGG GCC TGA AGG TCA GGG TCA CCC AAG CAA CAA
Ser Val Leu Ala End

Eco R I
AGT CCC GAG CAA TGA CCC GAA TTC
```

FIG.4C

Mouse adipsin cDNA

```
                                                              MboI      54
GTG CCT GCT GTC AGA ATG CAC AGC TCC GTG TAC TTC GTG GCT CTG GTG ATC CTG
            MET His Ser Ser Val Tyr Phe Val Ala Leu Val Ile Leu

81                                         BalI          108
GGA GCG GCT GTA TGT GCA GCA CAG CCC CGA GGC CGG ATT CTG GGT GGC CAG GAG
Gly Ala Ala Val Cys Ala Ala Gln Pro Arg Gly Arg Ile Leu Gly Gly Gln Glu 135                                                          162
GCC GCA GCC CAT GCT CGG CCC TAC ATG GCT TCC GTG CAA GTG AAC GGC ACA CAC
Ala Ala Ala His Ala Arg Pro Tyr MET Ala Ser Val Gln Val Asn Gly Thr His 189                                                          216
GTG TGC GGT GGC ACC CTG CTG GAC GAG CAG TGG GTG CTC AGT GCT GCA CAC TGC
Val Cys Gly Gly Thr Leu Leu Asp Glu Gln Trp Val Leu Ser Ala Ala His Cys 243                                                          270
ATG GAT GGA GTG ACG GAT GAC TCT GTG CAG GTG CTC CTG GGT GCC CAC TCC
MET Asp Gly Val Thr Asp Asp Ser Val Gln Val Leu Leu Gly Ala His Ser
```

FIG.5A

```
                                                                    324
CTG TCC GCC CCT GAA CCC TAC AAG CGA TGG TAT GAT GTG CAG AGT GTA GTG CCT
Leu Ser Ala Pro Glu Pro Tyr Lys Arg Trp Tyr Asp Val Gln Ser Val Val Pro
                        297                                         378
CAC CCG GGC AGC CGA CCT GAC AGC CTT GAG GAC AGC CTC ATT CTT TTT AAG CTA
His Pro Gly Ser Arg Pro Asp Ser Leu Glu Asp Ser Leu Ile Leu Phe Lys Leu
                        351                                         432
TCC CAG AAT GCC TCG TTG GGT CCC CAC GTG AGA CCC CTA CCC TTG CAA TAC GAG
Ser Gln Asn Ala Ser Leu Gly Pro His Val Arg Pro Leu Pro Leu Gln Tyr Glu
                        405                                         486
GAC AAA GAA GTG GAA CCC GGC ACG CTC TGC GAC GTG GCT GGT TGG GGT GTG GTC
Asp Lys Glu Val Glu Pro Gly Thr Leu Cys Asp Val Ala Gly Trp Gly Val Val
                        459                                         540
                        StuI
ACC CAT GCA GGA CGC AGG CCT GAT GTC CTG CAT CAA CTC AGA GTG TCA ATC ATG
Thr His Ala Gly Arg Arg Pro Asp Val Leu His Gln Leu Arg Val Ser Ile MET
                        513
```

FIG.5B

```
                                              567                                    594
AAC CGG ACA ACC TGC AAT CTG CGC ACG TAC CAT GAC GGG GTA GTC ACC ATT AAC
Asn Arg Thr Thr Cys Asn Leu Arg Thr Tyr His Asp Gly Val Val Thr Ile Asn 621                                    648
ATG ATG TGT GCA GAG AGC AAC CGC AGG GAC ACT TGC AGG GGA GAC TCC GGC AGC
MET MET Cys Ala Glu Ser Asn Arg Arg Asp Thr Cys Arg Gly Asp Ser Gly Ser 675                                    702
CCT CTA GTG TGC GGG GAT GCA GTC GAA GGT GTG GTT ACG TGG GGC TCT CGC GTC
Pro Leu Val Cys Gly Asp Ala Val Glu Gly Val Val Thr Trp Gly Ser Arg Val 729                                    756
TGT GGC AAT GGC AAA AAG CCG GGC GTC TAT ACC CGA GTG TCA TCC TAC CGG ATG
Cys Gly Asn Gly Lys Lys Pro Gly Val Tyr Thr Arg Val Ser Ser Tyr Arg MET

MboI                                          783                                    810
TGG ATC GAA AAC ATC ACA AAT GGT AAC ATG ACA TCC TGA GGG GAC ACC AGA GAC
Trp Ile Glu Asn Ile Thr Asn Gly Asn MET Thr Ser End

837
ACG TGG CTC AGG GAA ACA AGA GAC TGG CTC ACA ATA AAT GCA TGC ATC TG
```

FIG.5C

```
       NH2-MET Glu Lys Lys Ile Thr Gly Tyr Thr Thr Val Asp Ile Ser Gln Trp His Arg Lys Glu
           ATG GAG AAA AAA ATC ACT GGA TAT ACC ACC GTT GAT ATA TCC CAA TGG CAT CGT AAA GAA
                                       10                                    20

His Phe Glu Ala Phe Gln Ser Val Ala Gln Cys Thr Tyr Asn Gln Thr Val Gln Leu Asp
           CAT TTT GAG GCA TTT CAG TCA GTT GCA CAA TGT ACC TAT AAC CAG ACC GTT CAG CTG GAT
                           30                                    40

Ile Thr Ala Phe Leu Lys Thr Val Lys Asn Lys His Lys Phe Tyr Pro Ala Phe Ile
           ATT ACG GCC TTT TTA AAG ACC GTA AAG AAT AAG CAC AAG TTT TAT CCG GCC TTT ATT
                           50                                    60

His Ile Leu Ala Arg Leu MET Asn Ala His Pro Glu Phe Arg MET Ala MET Lys Asp Gly
           CAC ATT CTT GCC CGC CTG ATG AAT GCT CAT CCG GAA TTC CGT ATG GCA ATG AAA GAC GGT
                           70                                    80
```

FIG.7a-1

```
                                                              90                                100
Glu Leu Val Ile Trp Asp Ser Val His Pro Cys Tyr Thr Val Phe His Glu Gln Thr Glu
GAG CTG GTG ATA TGG GAT AGT GTT CAC CCT TGT TAC ACC GTT TTC CAT GAG CAA ACT GAA 110                               120
Thr Phe Ser Ser Leu Trp Ser Glu Tyr His Asp Asp Phe Arg Gln Phe Leu His Ile Tyr
ACG TTT TCA TCG CTC TGG AGT GAA TAC CAC GAT GAC TTC CGG CAG TTT CTA CAC ATA TAT 130                               140
Ser Gln Asp Val Ala Cys Tyr Gly Glu Asn Leu Ala Tyr Phe Pro Lys Gly Phe Ile Glu
TCG CAA GAT GTG GCG TGT TAC GGT GAA AAC CTG GCC TAT TTC CCT AAA GGG TTT ATT GAG 150                               160
Asn MET Phe Phe Val Ser Ala Asn Pro Trp Val Ser Phe Thr Ser Phe Asp Leu Asn Val
AAT ATG TTT TTC GTC TCA GCC AAT CCC TGG GTG AGT TTC ACC AGT TTT GAT TTA AAC GTG 170                               180
Ala Asn MET Asp Asn Phe Phe Ala Pro Val Phe Thr MET Gly Lys Tyr Tyr Thr Gln Gly
GCC AAT ATG GAC AAC TTC TTC GCC CCC GTT TTC ACC ATG GGC AAA TAT TAT ACG CAA GGC
─────────────────────────────────────────────────────────────────────────────────
CAT
```

FIG.7a-2

```
                                    190                          200
Asp Lys Val Leu MET Pro Leu Ala Ile Gln Val His His Ala Val Cys Asp Gly Phe His
GAC AAG GTG CTG ATG CCG CTG GCG ATT CAG GTT CAT CAT GCC GTT TGT GAT GGC TTC CAT

210
Val Gly Arg MET Leu Asn Glu Leu Gln Ser Asp Pro Glu Phe Glu
GTC GGC AGA ATG CTT AAT GAA TTA CAA CAG TCG GAT CCG GAA TTC GAA

230
Arg Ser Ser Cys Phe Gly Gly Arg MET Asp Arg Ile Gly Ala Gln Ser Gly Leu Gly Cys
CGC TCT TCT TGT TTC GGT GGT CGT ATG GAT CGT ATC GGT GCT CAA TCT GGT TTG GGT TGT
              220
Asn Ser Phe Arg Tyr-COOH
AAC TCT TTC AGA TAC
            240

CAT              hANP(102-126)
```

FIG.7a-3

DNA ENCODING HUMAN ADIPSIN WITH COMPLEMENT D ACTIVITY

CROSS-REFERENCE TO RELATED APPLICATION

This is a continuation-in-part of U.S. patent application Ser. No. 034,203, filed 2 Apr. 1987, now abandoned.

TECHNICAL FIELD

The invention relates to metabolic control and control of infection in animals and humans. More specifically, it relates to the regulation of adipose metabolism using a serine protease having complement D activity.

BACKGROUND ART

A murine model of obesity implicates the association of inadequate levels of a serine protease, designated adipsin, with obesity in mice. This protein is synthesized in and secreted from adipocytes, and synthesis of mRNA encoding this protein appeared specific to adipocytes (Zusalak, K. M., et al. *J Mol Cell Biol* (1985) 5:419). The levels of adipsin mRNA and adipsin protein in adipose tissue, as well as the level of adipsin protein circulating in blood, are lowered in obese animals.

More specifically, Flier, J. S., et al. *Science* (1987) 237:405–408 showed that the abundance of adipsin mRNA in adipose tissue was increased during fasting in normal rats and in the form of diabetes due to streptozotocin-induced insulin deficiency, but was decreased in a hyperglycemic, hyperinsulinemic state accompanied by increased adipose mass induced by a continuous infusion of glucose, as well as in strains of genetically obese mice. Adipsin mRNA was also shown to be reduced when obesity was induced by injection of monosodium glutamate to newborn mice. However, adipsin expression levels did not change in a model of obesity obtained simply by overfeeding normal rats. The relationship of both adipsin mRNA levels in adipocytes and adipsin protein levels in serum to obesity in mice, and in humans is disclosed and described in PCT application publication no. W088/07681, incorporated herein by reference.

The gene encoding adipsin in the murine system has been cloned and sequenced. Cook, K. S., et al. *Proc Natl Acad Sci USA* (1985) 82:6480–6484 obtained the sequence for a cDNA clone from murine 3T3 differentiating adipocytes which hybridizes to an mRNA that is induced at least 100-fold during differentiation and that encodes a protein of 28 kd having substantial homology to various serine proteases such as trypsin, chymotrypsin and elastase. The protein appears to be produced, however, in glycosylated 37 kd and 44 kd forms. The genomic sequence encoding this protein has also been retrieved (Min, H. Y., et al. *Nucleic Acids Research* (1986) 14:8879–8891) and the protein has been shown to be secreted into the circulation by adipose tissue and sciatic nerve (Cook, K. S., et al. *Science* (1987) 237:402–404).

Despite the recovery of the coding sequences, the murine protein has not been produced recombinantly, nor has the protein been prepared in pure form.

The complement system is also known to involve serine proteases, and the complete amino acid sequence of the serine protease complement protein D has been determined from the isolated protein (Niemann, M. A., et al. *Biochemistry* (1984) 23:2482–2486). The complement system is a complex interacting array of 20 proteins which, in the main, is activated by antigen/antibody interactions, specifically by binding of the Cl protein to immunoglobulins of the IgG and IgM class through its Clq subcomponent (*Bio Essays* (1986) 4:249–253). The result of activation of the complement cascade appears related to destruction of invading microbial hosts, but also to inflammation and, in some cases, to disease states such as arthritis.

In addition to the immune system-activated portion of the complement cascade, there is an alternate pathway in which the serine protease, complement D, is a participant. In this system, the alpha-chain of C3 (120 kd) is hydrolyzed to obtain C3a (9 kd) and C3b which is assembled with protein B to obtain C3bB, which is, in turn, hydrolyzed through the catalysis of complement factor D to obtain C3bBb. C3bBb catalyzes the hydrolysis of C3 to continue the cycle. Both C3a and C3b may directly interact with adipocytes or other cells related to fat metabolism. In addition, C3b can be further manipulated to obtain additional factors such as C5a and Ba which are also thus interactive.

Although the murine adipsin gene has been obtained, and synthetic peptides designed from the deduced amino acid sequence have been successfully used to obtain antibodies immunoreactive with circulating adipsin in mice, the human gene has not been available, nor are the murine antibodies generated to the synthetic peptides cross-reactive with human adipsin. Thus, the insights obtained with respect to murine metabolism have not, prior to this invention, been accessible to human systems. Furthermore, the purified murine protein has not been obtained. The present invention provides a DNA encoding a human protein which has both the energy regulating activity of adipsin and the macrophage lysis stimulation activity of complement factor D. The invention also provides purified murine adipsin.

The nexus between adipsin activity and complement D activity has not been suggested, although Mole, J. E., et al., in an abstract presented at the 12th International Complement Workshop, held 18–21 Sep. 1987, reported a partial cDNA clone for complement D which, when subjected to a computerized search, revealed a possible evolutionary relationship to the sequence reported for mouse adipsin, i.e., the cDNA complementary to the adipsin mRNA is induced during adipocyte differentiation.

Because serine proteases in general display a high degree of homology, homology alone does not necessarily lead one to conclude that the activity in assays for adipsin and for complement D would be shared. The present invention establishes these dual activities for this protein.

DISCLOSURE OF THE INVENTION

The invention provides methods and materials which make the findings and conclusions concerning the relevance of adipsin in the murine system accessible to humans, which provide purified recombinant murine adipsin, and which connect energy control and complement systems. The invention provides gene sequences, peptides, antibodies, and methods of using them which permit the diagnosis and control of obesity in human and other mammalian subjects and further provides protection for these mammals against bacteria, virus, and neoplastic cells.

Accordingly, in one aspect, the invention is directed to a DNA sequence encoding a human protein having adipsin and complement D activity. It is surprising that the DNA encoding this protein encodes both activities; both adipsin and complement D are serine proteases which would therefore be expected to be homologous, but not cross-reactive.

In other aspects, the invention is directed to expression systems capable of producing human or murine adipsin/complement D, to the methods to do so, to cells transformed with this expression system, to the recombinantly produced proteins, and to pharmaceutical compositions containing the human protein as active ingredient. In other aspects, the invention is directed to specific immunogenic fragments of the adipsin/complement D protein and to antibodies immunoreactive with this protein and/or the synthetic peptides representing these fragments.

The invention is also directed to methods to diagnose metabolically controlled obesity in humans or other mammals by measuring levels in blood or in adipose tissue of protein immunoreactive with the antibodies of the invention, or by measuring mRNA levels in adipose cells, and to methods to treat obesity or infection using pharmaceutical compositions containing the purified human protein. In another aspect, the invention is directed to control of obesity using components of the alternate complement pathway whose presence is mediated by the action of complement D, either directly or indirectly, such as C3a, Ba, or C5a, or fragments thereof.

BRIEF DESCRIPTION OF THE DRAWINGS

FIGS. 1A–C show the murine adipsin-encoding cDNA, including the complete signal sequence and the location of restriction sites used to obtain the 5' and 3' fragment probes.

FIGS. 2A–C show the DNA and deduced amino acid sequence for the insert of clone phg31, encoding human adipsin.

FIG. 3 shows a comparison of the amino acid sequence encoded by phg31 and the amino acid sequence determined from the protein of complement D.

FIGS. 4A–C show the modified phg31 sequence to complete the leader and shorten the 3' untranslated region.

FIGS. 5A–C show the sequence of murine cDNA as reported in Cook et al. (infra).

FIGS. 7a-1, 7a-3, and 7b illustrates the amino acid sequence and corresponding nucleotide sequences for a 241 amino acid (aa) CAT-hANP (from here on referred to as either CAT-hANP or CAT-hANF) hybrid protein, encoded by vector pChNF109. The amino terminal portion of this hybrid protein encodes the first 210 amino acids of CAT.

FIG. 7b illustrates the structure of mammalian expression vector pLEN, which contains a portion of the SV40 genome carrying transcription enhancer element, a segment of the human metallothionein gene carrying the transcription promoter and heavy metal regulatory elements, a BamHI cloning site for insertion of sequences to be expressed, and a portion of the human growth hormone gene carrying a polyadenylation signal.

MODES OF CARRYING OUT THE INVENTION

A. Human Adipsin/D

Figure 6:
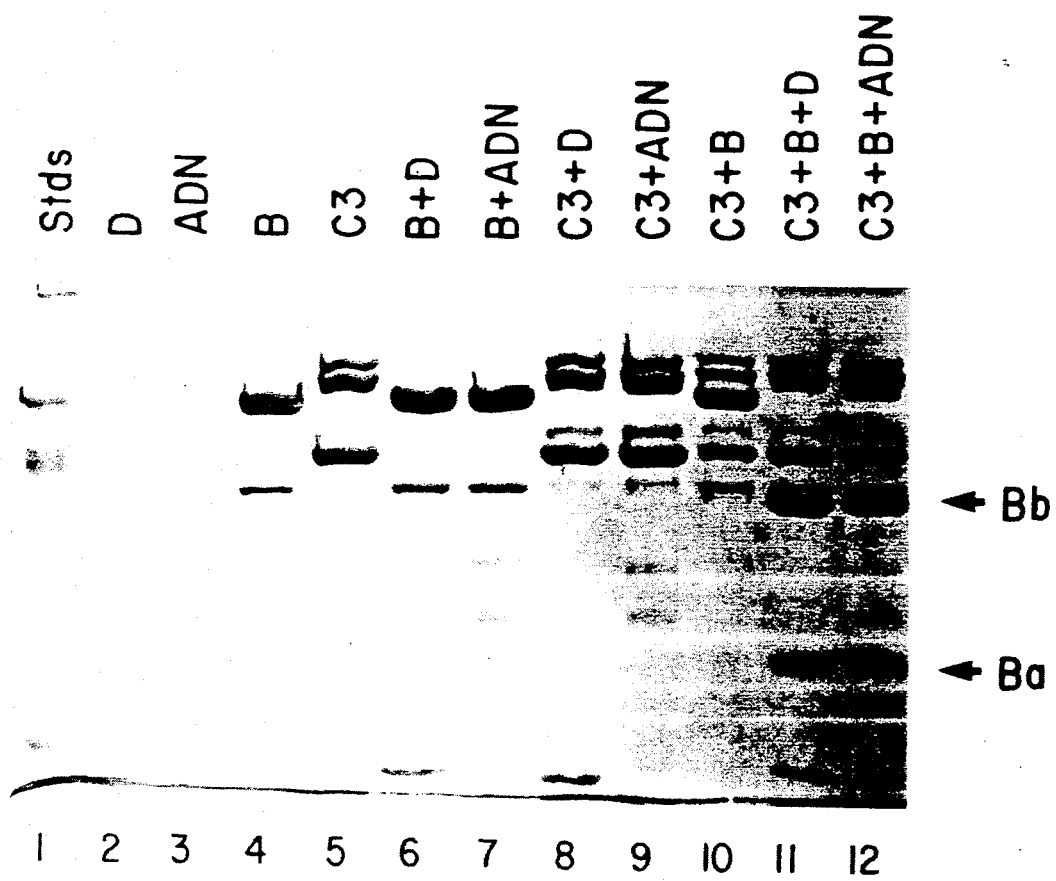
FIG. 6 shows the ability of murine adipsin to exhibit complement D activity.
Figure 7B:
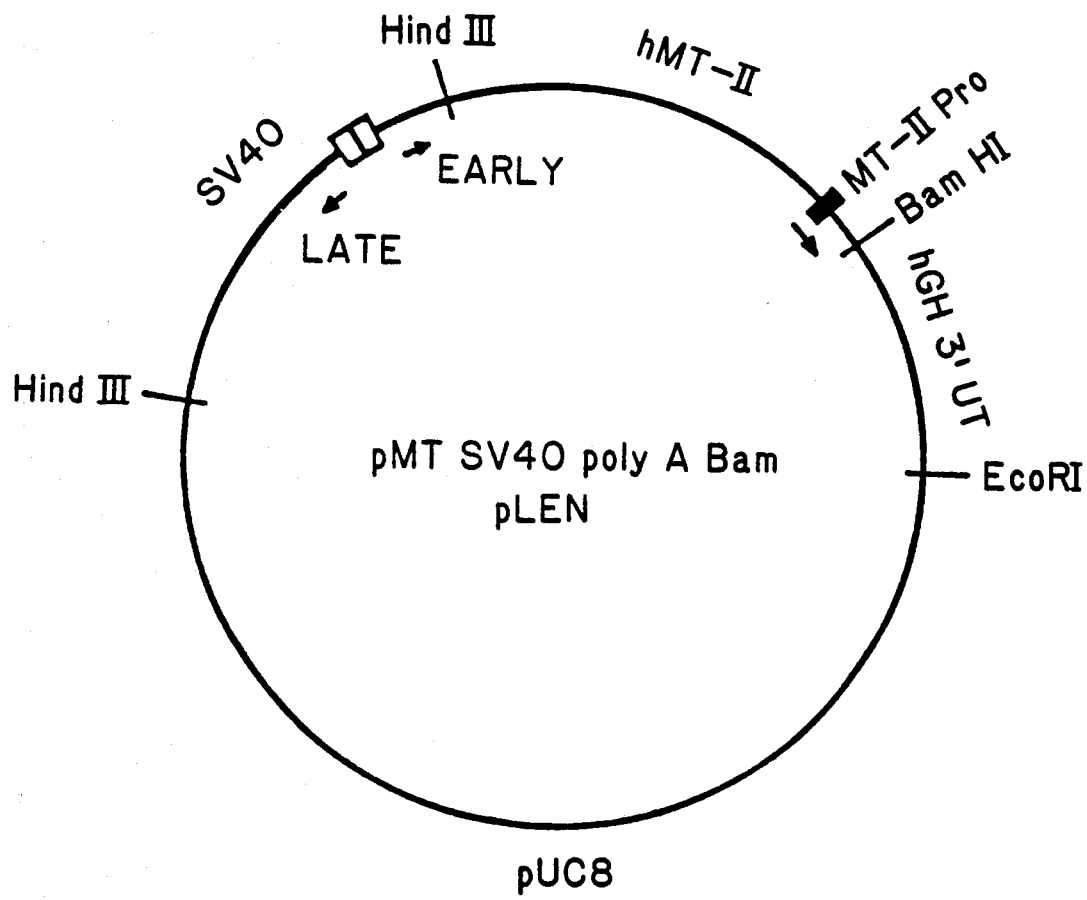

The invention provides means to obtain adequate quantities of a purified human protein having adipsin and complement D activities for use in therapy and to obtain antibodies for diagnosis; the availability of the purified protein permits generation of monospecific antibody preparations. Serum titers of this protein which are below normal indicate, in general, a metabolic deficiency, which metabolic deficiency leads to obesity. The level of adipsin in adipose tissue is also lowered in these individuals. In addition, levels of mRNA which hybridize to DNA encoding this protein are lowered in these individuals. Accordingly, this type of obesity can be distinguished from that caused simply by overeating.

The DNA encoding the human protein of the invention was recovered in isolated form from a human glioma cDNA library using the cDNA encoding the murine adipsin protein as a probe. Adipsin-encoding mRNA is also found in adipose tissue, and, as determined by the inventors herein, in macrophage extracts. It can also be prepared using standard synthetic techniques, based on the sequences disclosed herein. By "isolated form" is meant that the DNA referred to is obtained free of DNAs normally accompanying it. Of course, additional DNA may be in the composition such as untranslated sequences ligated to the coding sequence, or control sequences normally not associated with the coding sequence which have been added using standard genetic engineering techniques. In short, "isolated form" means simply that the claimed DNA is not in its native environment, nor is it a member of mixtures of DNAs obtained from the cell of its origin.

The DNA of the invention encodes a human protein having characteristics of both adipsin and complement D; herein designated human adipsin/D. By "adipsin activity" of the human protein is meant the ability of the protein to react with antibodies which are raised against and reactive with the protein having the amino acid sequence indicated as the mature adipsin protein in FIGS. 4A–C. This protein can be recombinantly produced in bacteria, mammalian cells, yeast, or a variety of other hosts. Additionally, fragments of the protein sequence shown in FIGS. 4A–C, can be used to raise antibodies which cross-react with human adipsin/D of the complete amino acid sequence shown, and, in general, these antibodies will react with members of the defined adipsin/D class. However, there may be some exceptions with regard to these subfragment antibodies, especially in instances where alterations in amino acid sequence result in different epitopes. By "adipsin activity" of the murine protein is meant ability to react with antibodies as described above related to the corresponding murine protein encoded by the cDNA of FIGS. 1A–C.

By "complement D activity" is meant the ability of the protein to effect the cleavage of purified human (or murine) Factor B of the complement pathway in the presence of purified, activated C3 in the standard complement assay illustrated in Example 7.

The protein encoded by the DNA which encodes the mature adipsin/complement D protein shown in FIGS. 4A–C is a preferred embodiment of the human protein of the invention. However, also included within the scope of the invention are proteins with amino acid sequences which differ somewhat from that illustrated in the figure but which retain the adipsin and complement D activities of this protein. Typically, the proteins will be over 60% homologous to the protein shown as mature adipsin/D in FIGS. 4A–C, preferably 80% or more homologous, and more preferably 90% or more homologous. Especially preferred are proteins having adipsin and complement D activity which are encoded by DNA sequences which are naturally occurring mutants of that shown in FIGS. 4A–C. Such mutants arise with some frequency, and the mutants can be isolated and sequenced using as probe the DNA sequence shown in FIGS. 4A–C under stringent conditions, since, in general, the mutations occur in only a few locations of the gene.

The DNA encoding the human adipsin/D protein is useful per se as a probe to assess the level of mRNA encoding adipsin as a measure of energy metabolism or to detect abnormalities in the genes of individuals having lowered levels of production of this protein.

B. Recombinant Production

The DNA sequence encoding the protein with adipsin and complement D activity can be modified so that the human (or murine) adipsin/D is produced recombinantly as an intracellular or as a secreted protein. In order to effect secretion, the DNA encoding the desired protein is fused to sequence encoding a signal sequence operable in the recombinant host cell chosen for production in such a manner that the signal sequence is operably linked to the mature protein when the gene is expressed. By "operably linked" is meant conjugated in such manner that the function of the component is preserved in the conjugate. Thus, in this instance, an "operably linked" signal sequence is one which is joined to the mature protein in such manner as to be capable of effecting the secretion of the mature form.

In order to produce the protein recombinantly, the adipsin/complement D-encoding sequences are constructed into expression systems wherein they are operably linked to control sequences which are capable of effecting the expression of the coding sequences when the system is transformed into a host wherein the control sequences are functional. By "control sequences" is meant DNA which is necessary or desirable to obtain expression of the gene, such control sequences invariably including promoters and, often, transcription terminating sequences; control elements to regulate expression, such as operators or enhancers; and sequences which are transcribed into mRNA portions helpful in translation, such as ribosome binding sites or CAP sites. The nature of the control elements in the expression system is understood to be a function of the host cell selected.

In the illustration below, the recovered gene of FIG. 3 was modified to facilitate expression, and the recombinant protein was obtained, in bacterial and mammalian cells. The availability of the DNA encoding the protein of the invention permits expression in a variety of hosts, including bacteria, yeast, mammalian cells, fungal cells, insect cells and, though perhaps less convenient, in plant cells. The variety of suitable promoters for hosts of various types is now considerable, and a number of options are available to the practitioner, such as the trp or penicillinase promoter in bacteria, promoters associated with the glycolytic pathways in yeast, viral promoters in insects and mammalian cells, and plant tumor promoters in plants. As is now well understood, the desired protein can be expressed either as a fusion protein or a mature protein which is intracellular or secreted. It is also understood that if the mature protein is produced as an intracellular protein, a preceding Met residue may be present on some or all of the molecules. Therefore, any sequences shown will be understood to have the possibility of including the N-terminal Met. However, this is invariably not present in secreted proteins.

The protein produced by recombinant cells is then purified using standard purification procedures appropriate to the medium from which the protein is to be isolated.

C. Utility

The human adipsin/D protein in isolated or partially purified form has a variety of utilities. The murine protein has similar uses in obtaining antibodies which are useful for diagnosis in human or other mammalian systems.

Diagnosis

For example, antibodies which are raised to human adipsin/D or to recombinant murine adipsin/D can be used as a diagnostic tool to determine whether the energy metabolism of a subject is abnormally skewed so as to predispose the subject to metabolically caused obesity. Such individuals are obese despite the ingestion of only a normal diet. However, as dietary habits are difficult to monitor, diagnosis of metabolic deficiencies using a laboratory test is a more reliable way to assess whether or not this energy usage aberration is present. Similarly to the murine model, humans and other mammals with aberrant energy metabolism show lower levels of adipsin in serum (and of adipsin-encoding mRNA in adipose tissue).

Thus, in one diagnostic approach, the proteins of the invention can be used as immunogens to generate antisera which are capable of immunoreaction with human or other mammalian adipsin. Alternatively, antibodies can be prepared by immunization using certain specific peptide subsequences of the human protein, such as Ser-Leu-Ser-Glu-Pro-Glu-Pro-Ser-Lys-Arg-Leu-Tyr-Asp (residues 59–71 in FIGS. 4A–C) or Ile-Val-Asn-His-Ala-Gly-Arg-Arg-Pro-Asp-Ser-Leu-Gln-His Leu-Gln-His (residues 130–143 of FIGS. 4A–C), suitably conjugated, if desired, to a neutral moiety, such as keyhole limpet hemocyanin, or the appropriate serum albumin, to render the peptide immunogenic. These peptides are used for illustration, but antigenic peptides can be designed based on deduced amino acid sequence of the human protein of the invention by taking advantage of the generally known three-dimensional configuration of serine proteases to discern surface regions of the protein as described by Cook, K. S., et al., *Science* (1987) 237:402–404; Greer, J., *J Mol Biol* (1981) 153:1027; Stroud, R. M., et al., *Cold Spring Harbor Symposium* (1971) 36:125. Design of fragments of murine adipsin for this purpose is described by Cook, K. S., et al. *Proc Natl Acad Sci USA* (1985) 82:6480; however, antibodies raised to these murine fragments are not immunoreactive with human adipsin/D. Thus, by using standard techniques for predicting regions of immunogenicity, and, in addition, aided by knowledge of three-dimensional structure, suitable fragments can be determined for the particular protein encoded.

The antibody preparations thus obtained, which can be high titer antisera or monoclonal preparations obtained by immortalizing the immunoglobulin-producing cells, are useful in the diagnosis of adipsin deficiency type obesity. In conducting the tests, the serum or plasma of the subject to be tested is reacted with the antibodies, and the specific interaction of antibody with adipsin is detected by suitable labeling. Similar tests can be conducted using biopsied adipose tissue, which can be homogenized and tested by standard immunoassay procedures, as well as extracted into SDS sample buffer and subjected to Western blot. A wide variety of protocols is available in the art for conduct of immunoassays, and the manner of conducting them is within the skill of the ordinary practitioner. For example, the prepared antibodies might be adhered to a solid surface such as a microtiter well. The sample of plasma, serum or homogenized tissue is then added to the well, and nonbinding components washed away. The presence of the adipsin bound to the well is then detected using a second sample of antiserum which is labeled with a detectable label such as, for example, a radioisotope, a fluorescent moiety, an enzyme, or chromophore. In the alternative, since large quantities of adipsin are made available by the invention, a competition assay can be conducted in which the adipsin in the sample to be tested competes with labeled adipsin bound to supported antibody.

It should be again noted that the murine antibodies described by Flier et al. (*Science* (1987) 237:405-408), prepared using fragments of the murine protein, are not cross-reactive with human adipsin. However, antibodies raised against full-length murine adipsin do cross-react with the mature human adipsin/D shown in FIG. 3.

Alternatively, the DNA encoding human adipsin/D which is recovered from cDNA or from the genome can be used as a probe to diagnose the levels of the relevant adipsin encoding mRNA adipose tissue as a method to assess metabolic deficiencies in obese subjects. The conditions of such hybridization probing are described by Spiegelman, M., et al. *J Biol Chem* (1983) 258:10083. In this method, the probes are radiolabeled by random priming and autoradiograms are scanned by laser densitometry. Other labeling methods can also be used. In addition, partial cDNAs or synthetic oligomeric probes having sequences of portions of the cDNA or genomic DNA can also be used.

Therapy

The recombinant human adipsin/D purified from the cultures of recombinant hosts can also be formulated into convenient dosage forms for therapeutic use in the treatment of forms of obesity associated with adipsin deficiency in humans and other mammals. The preferable mode of administration is by injection (preferably IV, but IM, subcutaneous (into fat tissue) and IP can be used) and the protein is thus formulated in a manner suitable for this mode of administration, such as suspension or solution in buffer, or in Hank's or Ringer's solution, or prepared in solid form to be taken up in solution when use is desired. Alternatively, systemic administration can be effected using slow release devices, transmembrane excipients, e.g., nasal delivery, or transdermal penetrating materials.

The amounts to be administered depend, of course, on the condition of the patient and the judgment of the practitioner. Suitable dosage levels are defined to maintain the proteins levels in blood at approximately normal values—i.e., on the order of 1 ug/ml blood. The quantities administered will depend on the extent of the deficiency in the subject and on the capability of the administered protein to be cleared. For IV administration dosages in the range of 100 ug-100 mg are appropriate. For injection into fat tissue typical doses are 10 ug-5 mg. The protein is continuously or semicontinuously administered to offset the deficiency, and the dosage adjusted to the individual patient, much as is the case with insulin.

In view of the nexus between complement D and adipsin activities, the mediators which are formed as a result of complement D activity are also useful in regulating the metabolic state managed by adipsin levels. For example, C5a and C3a, which are approximately 70-amino acid peptides of known sequence, are mediators which are formed by virtue of the operation of the complement D-based alternate pathway of the complement cascade. In addition, Ba, a 30 kd protein, is released when C3bB is lysed by complement D. These mediators are readily available and can be administered in a manner similar to that described above for adipsin/D for the regulation of obesity and other energy-associated metabolic functions. Other mediators involved in the alternate complement pathway as a direct or indirect result of complement D activity can also be used. In all cases, use of subfragments of these mediators is preferred as many mediators are anaphylatoxins.

The complement D alternate pathway is involved in the generation of factors which stimulate macrophage to lyse unwanted materials which are nonbenign in character and include infective agents such as bacteria, parasites, and viruses, and also neoplastic tissue. Accordingly, the pharmaceutical compositions containing the protein of the invention are useful in treating or preventing infection, especially bacterial infections which are directly controlled by the alternate complement D branch of the complement cascade. It is known that persons deficient in complement D are susceptible to bacterial infection, although their resistance to viral infection appears normal. However, as complement D is instrumental in generating the macrophage-mediated lysis of a variety of objectionable materials, the protein of the invention is useful in eliminating these nonbenign materials in general. For this use, a preferable mode of administration is intravenous in standard excipients at about 1-5 times the normal circulating levels which are about 1 ug/ml in serum.

Furthermore, in view of the ability of the complement system to opsonize immune complexes, stimulants of the complement system, such as the protein of the invention, are useful in treating autoimmune diseases such as lupus erythrymatosis and rheumatoid arthritis. These diseases are associated with the immune complexes formed against indigenous tissue which are associated with lysis generated by the classical portion of the complement cascade. Stimulation of the alternate pathway with additional protein with complement D activity assists in the removal of these unwanted immune complexes.

As described in the administration for treatment of obesity, the protein, when administered to employ its complement D activity, can be administered systemically, including intravenous, intramuscular, and intraperitoneal injections, or by using other modes of systemic administration, such as nasal delivery, or, if used to treat a localized infection, such as in a wound, a topical or local administration can also be employed.

The following examples are intended to illustrate but not to limit the invention.

Example 1

Human cDNA Encoding Adipsin

A lambda-gt11 library representing the reverse transcript of RNA from human glioma, ATCC HTB138, was obtained from ClonTech, Palo Alto, Calif. The original cell line was isolated from a 76 year old caucasian male and grown as a monolayer to give fibroblast-like cells which are hypotetraploid. From the gt11 library, 1.5 million plaques were lifted in duplicate onto nylon filters (Amersham-Hybond-N) and hybridized with mouse adipsin probes in 30% formamide, 5×SSPE, 5×Denhardt's, at 42° C. The filters were washed in 2×SSC, 0.1% SDS at 50° C. The probes were the 5' BamHI/StuI fragment of the murine cDNA, and the 3' StuI/BamHI fragment of this sequence as shown in FIGS. 1A-C.

Three positive plaques which hybridized to both probes were characterized by sequence analysis, and subcloned into pUC9 or pBR322 to obtain phg26, phg31, and phg40. The approximately 1.1 kb insert in phg31 (cloned into pUC9) is shown in FIGS. 2A-C. This fragment encodes the complete amino acid sequence of the mature protein, starting at the position shown as amino acid number 1 in the figures with the N-terminal sequence Ile-Leu-Gly-Gly . . . , and most of the signal sequence. The insert also contains the long 3' untranslated sequence shown in FIGS. 2A-C, which shows the entire phg31 insert.

A comparison of the amino acid sequences of the protein encoded by the gene of the phg31 insert, obtained by hybridization to murine adipsin cDNA and the published amino acid sequence of complement D is shown in FIG. 3. It is believed discrepancies are due to sequencing errors in the complement D protein. There are no glycosylation sites in these proteins.

Example 2

Preparation of Expression Vectors

The insert in phg31 was modified to truncate the 3' untranslated region and to complete the signal sequence. The shorter 3' untranslated sequence of phg40 (cloned into pBR322) was exchanged with that of phg31 by ligating the 5' EcoRI/PstI fragment of phg31 with the 3' PstI/EcoRI fragment of phg40 to obtain phg31/40. The resulting insert with a shorter 3' sequence is shown in FIGS. 4A-C. As phg40 was obtained by cloning into the EcoRI site of pBR322 rather than pUC9, the exchanged portion contains the included pBR322 HindIII site just upstream of the 3' end.

The 5' signal sequence shown in FIGS. 4A-C was completed using synthetic oligonucleotides by cleaving the insert at the NotI site, shown in FIGS. 2A-C, and extending, with synthetic oligonucleotides, to the BamHI site shown in FIGS. 4A-C. The oligos used to construct the signal were designed based on analogy to the known mouse signal sequence, and the result is shown in the figure.

The modified insert of phg31/40 was then used to construct an expression system by ligation into the mammalian expression vector pLEN. The construction of pLEN is described below.

The finished insert after excision from phg31/40 and ligation into BamHI/EcoRI-cleaved pLEN is shown in FIGS. 4A-C. This places the inserted fragment under the control of the metallothionein promoter and SV40 enhancer and provides for amplification by heavy metal addition due to the inclusion of the MT-II gene. The finished vector is designated pLEN:hg31/40.

To construct the analogous vector for the murine adipsin, the murine cDNA shown in FIGS. 5A-C (disclosed in Cook, K. S., et al, *Proc Natl Acad Sci USA* (1985) 82:6480-6484) was digested with MboI. The following oligos were ligated onto the 5' end to recreate the first 11 amino acids of adipsin and to provide a BamHI site:

```
         10         20         30         40
GATCCCACCA TGCACAGCTC CGTGTACTTC GTGGCTCTGG T
     GGTGGT ACGTGTCGAG GCACATGAAG CACCGAGACC ACTAG
```

The following oligos were ligated onto the 3' end to recreate the carboxyl terminal 11 amino acids of adipsin, provide polylinker sequences and a BamHI site:

```
       10         20         30         40         50
GATCGAAAAC ATCACAAATG GTAACATGAC ATCCTGAGGG GATCCCCGGG
    CTTTTG TAGTGTTTAC CATTGTACTG TAGGACTCCC CTAGGGGCCC
60
AATTCTATGC TG
TTAAGATACG ACCTA
```

The recreated adipsin cDNA was ligated into BamHI-digested pLEN to obtain pLEN:MuAd/D.

Bacterial expression vectors are obtained by fusing the DNA encoding the mature human and murine protein-encoding DNAs into the vector pChNF109 to replace a contained coding sequence for a protein.

The construction of pChNF109 is described below. The constructions for the human adipsin/D were made by isolating the EcoRI/StyI fragment from phg31/40 and inserting this fragment into EcoRI/HindIII-cleaved pChNF109 using linkers at the 3' end. To insert the human adipsin/D DNA, phg31-40 is digested with EcoRI and StyI, and pChNF109 is digested with EcoRI and HindIII. EcoRI digestion cleaves phg31/40 at the EcoRI site in the polylinker derived from pUC8; the StyI site is adapted to the HindIII site of the vector using the linker:

```
5' CTA GGG TGC CGG GGC CTG A 3'
3'     CC ACG GCC CCG GAC TTC GA 5'
```

The digestion of pChNF109 with EcoRI/HindIII removes amino acids 74-210 of the CAT sequence, and all of the ANF-coding sequences (see below). The finished vector is designated bobCAT:hg31/40.

To obtain the corresponding murine vectors, the pLEN:MuAd/D was digested with BalI and MboI. The following oligos were ligated onto the 5' end to recreate 4 amino terminal amino acids and provide an EcoRI site:

```
          10
AATTCATTCT GGG
    GTAAGA CCC
```

The following oligos were ligated onto the 3' end to recreate the carboxy terminal 11 amino acids and to provide a transcription termination signal and a HindIII site:

```
      10         20         30        40
GATCGAAAAC ATCACAAATG GTAACATGAC ATCCTGA
    CTTTTG TAGTGTTTAC CATTGTACTG TAGGACTTCG A
```

The resulting murine sequence was ligated into EcoRI/HindIII digested pChNF109 to obtain bobCAT:MuAd/D.

Host Vectors

Bacterial Vectors

The host vector providing the bobCAT expression system, pChNF109, is prepared as follows. This vector contains codons for chloramphenicol acetyl transferase (CAT) and EcoRI and HindIII cloning sites for insertion of genes in reading frame with the CAT sequence, as well as a coding insert for a different protein. pChNF109 encodes a 241 amino acid CAT-hANF hybrid protein containing an endoproteinase Glu-C proteolytic cleavage site. The DNA and encoded amino acid sequences of CAT and hANF are shown in FIGS. 7a-1, 7a-2, 7a-3. Most of the CAT gene (amino acids 1–210) has been joined in-frame to the hANF(102-126) gene and cleavage site (26 amino acids) through a linker sequence (5 amino acids). This vector was constructed from plasmids pTrp233, pCAT21, and phNF75, which supplied the plasmid backbone and trp promoter-operator, and CAT gene, and the hANF(102-126) gene and cleavage site, respectively.

Plasmid pTrp233 was described in W087/06588. Plasmid pCAT21 was constructed by insertion of the CAT gene (from transposon Tn9; Alton and Vapnek (1979) 282:864–869) into pTrp233 under the control of the trp promoter-operator. Plasmid pAL13ATCAT (a plasmid containing Tn9, disclosed in copending U.S. Ser. No. 095,742, filed 11 Sep. 1987, and incorporated herein by reference) was digested with NdeI and HindIII and the approximately 750 bp NdeI-HindIII fragment containing the CAT gene (with the initiating Met residue encoded at the NdeI site) was purified using agarose gel electrophoresis. The CAT gene was ligated with NdeI/HindIII-digested pTrp233 using T4 DNA ligase, and the resulting plasmid pCAT21 was isolated from *E. coli* MC1061.

Plasmid phNF75 was constructed by insertion of a synthetic hANP gene preceded by a proteolytic cleavage site into plasmid pBgal (Shine et al, *Nature* (1980) 285:456). Eight oligodeoxyribonucleotides were assembled into a synthetic hANF(106-126) gene preceded by an endoproteinase Glu-C cleavage site. The synthetic gene was ligated into BamHI-digested pTrp233. A plasmid with the insert in the orientation which gives adjacent HindIII, BamHI and EcoRI sites at the 3' end of the hANP gene, phNF73, was identified by the size of the fragments generated by digestion with HindIII and PvuII. Plasmid phNF73 was digested with EcoRI, the hANP gene purified using polyacrylamide gel electrophoresis, and the gene ligated into EcoRI-digested pBgal to obtain phNF75.

pChNF109 was constructed by insertion of DNA fragments containing CAT, hANF and the proteolytic cleavage site, and a linker sequence into plasmid pTrp233. Plasmid phNF75 was digested with EcoRI and HindIII, the approximately 80 bp EcoRI-HindIII fragment containing hANF was purified by polyacrylamide gel electrophoresis and ligated into EcoRI/HindIII-digested pTrp233 to obtain phNF87. pCAT21 was digested with ScaI, and BamHI synthetic linkers (5'-CGGATCCG-3') were attached to the blunt termini. The ligation was digested with BamHI and the approximately 740 bp BamHI fragment was purified by agarose gel electrophoresis. The BamHI cassette and BamHI-digested plasmid phNF87 were ligated to obtain pChNF109 having the CAT gene fused in-frame to the endoproteinase Glu-C cleavage site followed by the hANF gene.

Mammalian Vectors

The host plasmid pLEN contains the SV40 enhancer upstream of the MT-II promoter and about 600 bp of the 3' untranslated region termination sequence associated with human growth hormone. Construction of this host vector uses the following sources:

MT-II: The plasmid pHSI contains 840 bp of the hMT-II sequence from p84H (Karin, M., et al. *Nature* (1982) 299:297–302) which spans from the HindIII site at position −765 of the hMT-II gene to the BamHI cleavage site at base +70. Plasmid p84H was digested to completion with BamHI, treated with exonuclease Bal-31 to remove terminal nucleotides, and then digested with HindIII. The desired 840 bp HindIII/blunt fragment was ligated into pUC8 (Vieira, J., et al. *Gene* (1982) 19:259–268) which had been opened with HindIII and HincII digestion. The ligation mixture was transformed into *E. coli* HB101 to Amp®, and one candidate plasmid, designated pHSI, was isolated and sequenced by dideoxy sequencing. pHSI contains the hMT-II control sequences upstream of a polylinker containing convenient restriction sites.

hGH Termination Sequences: Genomic sequences encoding hGH were isolated from p2.6-3 (DeNoto et al. *Nucleic Acids Res* (1981) 19:3719) by digestion with BamHI, which cuts at the 5' end of the first exon, and EcoRI, which cuts 3' of the functional gene, followed by polyacrylamide gel purification. The isolated fragment was ligated into BamHI/EcoRI-digested pHSI and the ligation mixture transformed into *E. coli* MC1061 to Amp®. Successful transformants were screened by restriction analysis, and a strain containing the desired plasmid, designated pMT-hGHg, was further propagated to prepare quantities of plasmid DNA.

Enhancer: A pair of host expression vectors containing the SV40 enhancer in operable linkage with the MT-II promoter and the 3' untranslated sequences from hGH was constructed by inserting an 1120 bp SV40 DNA fragment into the HindIII site preceding the MT-II promoter sequences in pMT-bGHg. The SV40 DNA fragment spans the SV40 origin of replication and includes nucleotide 5171 through nucleotide 5243 (at the origin), the duplicated 72 bp repeat from nucleotide 107 to 250, and continues through nucleotide 1046 on the side of the origin containing the 5' end of late viral mRNAs. This HindIII 1120 bp fragment is obtained from a HindIII digest of SV40 DNA (Buchman, A. R., et al. *DNA Tumor Viruses*, 2d ed. (J. Tooze, ed.), Cold Spring Harbor Laboratory, New York (1981), pp. 799-841), and cloned into pBR322 for amplification. The cloning vector was cut with HindIII and the 1100 bp SV40 DNA fragment isolated by gel electrophoresis and ligated into HindIII-digested, CIP-treated, pMT-hGHg. The resulting vectors, designated phGHg-SV(9) and phGHg-SV(10), contain the fragment in opposite phGHg-SV(9), the enhancer is about 1600 bp from the 5' mRNA start site; in the opposite orientation, it is approximately 980 bp from the 5' mRNA start site. Both orientations are operable, but the orientation wherein the enhancer sequences are proximal to the start site provides higher levels of expression. It is believed that deletions which place the enhancer 250-400 bp upstream of the transcription start are optimal.

Completion of pLEN: phGHg-SV(10) was digested with SmaI, and BamHI linkers were ligated onto the SmaI site. The vector was then digested with BamHI (which removes the growth hormone gene) and religated, yielding pLEN. pLEN contains the approximately 600 bp of the growth hormone 3' untranslated region containing the polyadenylation site, the SV40 enhancer, and the MT-II promoter.

Example 3

Expression of DNA Encoding Murine and Human Adipsin/Complement D

Recombinant protein was obtained by transfecting the murine adipsin/D expression vector pLEN:-MuAd/C into CHO cells along with pSV-Neo as a selection means. Selected cells were then cultured to a high cell count, and the metallothionein promoter induced by the addition of zinc ion.

The murine adipsin/D protein produced in the CHO cells was purified from the conditioned medium, as follows:

3.5 liters of conditioned medium was brought to 50% saturation with solid ammonium sulfate at 4° C. and spun at 6,500 g for 90 minutes. The supernatant is decanted through cheesecloth and brought to saturation with solid ammonium sulfate. It is then spun 2 hours at 6,500 g and the supernatant poured carefully off. The red precipitate was resuspended in a total of 60 ml, 100 mM NaCl, 50 mM Tris, pH 7.5, and dialyzed exhaustively against 3×4 liters of the same.

The sample was spun 15 minutes×3000 g to remove particulates and applied to a 40 ml column of ConA Sepharose (Sigma) equilibrated with 100 mM NaCl, 50 mM Tris, pH 7.5. The columns was washed with buffer until no protein was detectable in the flowthrough (about 200 ml). The column was eluted with 0.5M alpha-methylmannoside in 100 mM NaCl, 50 mM Tris, pH 7.5. Fractions containing the recombinant protein run out on SDS-PAGE and visualized by silver staining. Factions containing protein of correct M.W. were pooled and dialyzed exhaustively against 20 mM NaCl, 50 mM Tris, pH 7.5.

Dialyzed protein was spun 15 minutes at 3000 g and applied to a Waters DE-41 HPLC column at a flow rate of 1 ml/min. The column was washed with 20 mM NaCl, 50 mM Tris, pH 7.5, until the $A_{280}<0.01$. The column was then eluted at 1 ml/min with a linear 40 minute gradient of 0-35% 1M NaCl, 50 mM Tris, pH 7.5. The protein peak elutes at about 12-16% high salt solvent. Content of the fractions in the desired protein was determined by PAGE.

In a similar manner, the human protein-encoding vector, pLEN:hg31/40, is transfected into CHO cells along with pSV-Neo, and cultured under conditions which activate the MT-II promoter. The secreted protein can be purified in a manner similar to that set forth above for the murine counterpart, except that the lectin-affinity column is inappropriate for the human protein, in that the human protein contains no glycosylation sites and is thus free of carbohydrate sidechains to impart affinity with respect to lectin. In lieu of the ConA column, therefore, an affinity column using antibodies immunoreactive with the human protein can be used. In the alternative, the method used to purify human complement D, as described in Neimann, M. A., et al. *Biochemistry* (1984) 23:2482-2486 (supra) can be used.

For bacterial expression, the bobCAT:hg31/40 and bobCAT:MuAd/D vectors are transformed into MM294 cells, and the trp promoter induced by the addition of IAA. Inclusion bodies are isolated, and the fusion proteins are isolated from the inclusion bodies using standard techniques.

Example 4

Production of Antibodies

Antibodies immunoreactive with the human adipsin/D are prepared by using standard immunization protocols in rabbits and recovering the antisera. In addition, antibody-secreting cells from the immunized animals can be immortalized using fusion techniques to produce hybridomas which can then be screened for antibodies immunoreactive with the recombinantly produced human protein. Antibodies immunoreactive with human adipsin/D can be produced by immunization with the recombinantly produced murine or human adipsin/C or with certain specific fragments of the human protein, as set forth above.

Example 5

Therapeutic Formulations

Human adipsin/D, produced as in Example 3, is dissolved in physiological saline, pH 7.4, at a concentration of 5 mg/ml for intravenous infusion.

Example 6

Determination of Adipsin in Serum

Sera from individuals suspected of having poor energy balance due to adipsin deficiency are assayed for the presence of this protein by a competition assay using the recombinantly produced protein labeled with $^{125}I$ using the (chloramine T) method. The sera with measured amounts of labeled human adipsin/D are treated with antibody prepared as in Example 4 and the antibody-bound fraction is separated by adsorption to protein A sepharose.

The level of radioactivity remaining in the supernatant varies inversely with the level of adipsin in the serum. The absolute amount is determinable by comparison to a standard curve.

Example 7

Complement D Activity of Mouse Adipsin

The ability of mouse adipsin to mimic complement D was tested in an in vitro assay by monitoring the cleavage of purified human factor B (93 kd) to Bb (63 kd) and Ba (30 kd) in the presence of purified, suitably activated, C3 (alpha subunit 120 kd, beta subunit 80 kd). The reactions were conducted in 30 ul 50 mM Tris, pH 7.3, 75 mM NaCl, 1 mM MgCl$_2$, at 37° C. 10 ng of either complement factor D or mouse adipsin were added to the test samples; controls were run using no addition. 3 ul of each reaction mixture was run on a 10% polyacrylamide SDS gel and silver stained. The results are shown in FIG. 6. As shown in the Figure, B was cleaved to Bb and Ba in the presence of C3 with the addition of either D or adipsin. In the figure, Lane 1 contains size markers.
Lane 2 contains 100 ng factor D.
Lane 5 contains 150 ng C3.
Lane 4 contains 150 ng factor B.
Lane 10 contains C3 plus factor B.
Lane 6 contains factor B plus D.
Lane 7 contains factor B plus adipsin.
Lane 8 contains C3 plus D.
Lane 9 contains C3 plus adipsin.
Lane 11 contains C3 plus B plus D incubated for ½ hour.
Lane 12 contains C3 plus B plus adipsin, also incubated for ½ hour.

We claim:

1. A recombinant DNA sequence in isolated form which encodes a human protein as shown in FIG. 3 having adipsin and complement D activity.

2. The DNA sequence of claim 1 wherein said protein has the amino acid sequence encoded by DNA shown as encoding mature protein in FIG. 3 or a naturally occurring mutant DNA sequence thereof.

3. The DNA sequence of claim 1 which further includes an upstream DNA sequence which encodes the signal sequence natively associated with said human protein in operable linkage with said protein.

4. The DNA sequence of claim 3 wherein the signal sequence is that encoded by codons comprising codons −1 through −24 of FIG. 3.

5. A recombinant expression system which comprises DNA sequence encoding a human protein as shown in FIG. 3 having adipsin and complement D activity operably linked to control sequences, which expression system is capable of effecting the expression of said protein-encoding DNA sequence when transformed into a host cell.

6. A recombinant host cell transformed with the expression system of claim 5.

7. The recombinant host cell of claim 6 which is mammalian.

8. The recombinant host cell of claim 6 which is yeast.

9. The recombinant host cell of claim 6 which is bacterial.

* * * * *

UNITED STATES PATENT AND TRADEMARK OFFICE
CERTIFICATE OF CORRECTION

PATENT NO. : 5,223,425

DATED : Jun. 29, 1993

INVENTOR(S) : Jeffrey S. Flier, Bruce M. Spiegelman, Barry M. Rosen, and R. Tyler White It is certified that error appears in the above—identified patent and that said Letters Patent is hereby corrected as shown below:

Col. 13, line 12, after "opposite" insert --orientations preceding the MT-11 promoter. In--.

Signed and Sealed this

Fifteenth Day of March, 1994

Attest:

BRUCE LEHMAN

Attesting Officer  Commissioner of Patents and Trademarks